United States Patent
Baier (12)

(10) Patent No.: US 6,245,518 B1
(45) Date of Patent: Jun. 12, 2001

(54) POLYNUCLEOTIDE ARRAYS AND METHODS OF MAKING AND USING THE SAME

(75) Inventor: Joerg Baier, Foster City, CA (US)

(73) Assignee: Hyseq, Inc., Sunnyvale, CA (US)

( * ) Notice: Subject to any disclaimer, the term of this patent is extended or adjusted under 35 U.S.C. 154(b) by 0 days.

(21) Appl. No.: 09/454,822

(22) Filed: Dec. 6, 1999

Related U.S. Application Data

(60) Provisional application No. 60/111,961, filed on Dec. 11, 1998.

(51) Int. Cl.[7] .............................. C12Q 1/68; C12P 19/34; C07H 21/04
(52) U.S. Cl. ......................... 435/6; 435/91.2; 536/24.33
(58) Field of Search .................... 435/6, 91.2; 536/23.1, 536/24.33

(56) References Cited

U.S. PATENT DOCUMENTS

| | | |
|---|---|---|
| 5,424,186 | 6/1995 | Fodor et al. . |
| 5,445,934 | 8/1995 | Fodor et al. . |
| 5,578,832 | * 11/1996 | Trulson et al. .................... 250/481.1 |
| 5,695,940 | * 12/1997 | Drmanac et al. ......................... 435/6 |
| 5,723,591 | 3/1998 | Livak et al. . |
| 5,744,305 | 4/1998 | Fodor et al. . |
| 5,822,472 | 10/1998 | Danielzik et al. . |

FOREIGN PATENT DOCUMENTS

| | | |
|---|---|---|
| WO 90/03382 | 4/1990 | (WO) . |
| WO 98/31836 | 7/1998 | (WO) . |

OTHER PUBLICATIONS

Lockhart et al., "Expression monitoring by hybridization to high–density oligonucleotide arrays, " *Nature Biotechnology*, 1996, vol. 14, pp. 1675–1680.*
Constantine et al., "Use of GeneChip high–density oligonucleotide arrays for gene expression monitoring," *Life Science News*, 1998, pp. 11–14.*
Fodor et al. 1991, "Light–Directed, Spatially Addressable Parallel Chemical Synthesis," *Science* 251:767–73.
Pease et al. 1994, "Light–generated oligonucleotide arrays for rapid DNA sequence analysis," *Proc. Natl. Acad. Sci. USA* 91:5022–5026.

* cited by examiner

Primary Examiner—John S. Brusca
Assistant Examiner—Young Kim
(74) Attorney, Agent, or Firm—Pennie & Edmonds LLP

(57) ABSTRACT

The present invention relates to methods of using labeled tracers to generate spatially addressable arrays of immobilized molecules, particularly polynucleotides, that can be normalized for differences in immobilization efficiencies at different addresses in the array. It also relates to the arrays generated by the method and to use of these arrays to enhance discrimination in array-based assays, particularly the discrimination between perfectly matched hybrids and hybrids containing a single mismatch in nucleic acid hybridization assays.

33 Claims, 2 Drawing Sheets

POLYNUCLEOTIDE ARRAYS AND METHODS OF MAKING AND USING THE SAME

This application claims the benefit of the Provisional Patent Application entitled, "IMPROVED POLYNUCLEOTIDE ARRAYS AND METHODS OF MAKING AND USING THE SAME," Ser. No. 60/111,961, filed Dec. 11, 1998.

1. FIELD OF THE INVENTION

The present invention relates to spatially-addressable arrays of molecules, particularly biological molecules such as peptides and oligonucleotide probes, and methods of making and using the same.

2. BACKGROUND OF THE INVENTION

Recent advances in the ability to construct arrays of biological molecules has greatly facilitated the ease and speed with which certain biological assays can be performed. For example, in the areas of nucleic acid sequencing and analysis, the advent of new technologies for constructing arrays of immobilized target nucleic acids or oligonucleotide probes has enabled the rapid screening and sequencing of nucleic acids. Arrays of peptides and small biomolecules have also proven useful in binding assays used in pharmaceutical development. The usefulness of these arrays depends on the ability to generate arrays with spatially addressable regions of defined composition or sequence.

Several technologies have been developed for producing these arrays of biological molecules. Several researchers have devised methods for in situ synthesis of arrays of biological polymers, such as nucleic acids, peptides, and carbohydrates. These methods use, for example, physical barriers to separate regions, devices (such as inkjet printers) for precise delivery of reagents to regions, or masking techniques that allow the use of light to determine the course of synthesis. See, e.g., WO 90/03382; Fodor et al., 1991, Science 251:767–73; Pease et aL., 1994, Proc. Natl. Acad. Sci. 91:5022–26; U.S. Pat. No. 5,424,186, to Fodor et al. Alternatively, presynthesized biomolecules or biological polymers may be attached directly to the substrate at precise positions using a variety of techniques, ranging from simple spotting to robotic delivery systems. A variety of different substrates and techniques for attaching the biomolecules to the substrates are also available.

As noted above, arrays of nucleic acids have proven particularly valuable. The ability to perform many previously available techniques has been greatly enhanced by availability of arrays, which permit many assays to be performed simultaneously on a single array rather than having to do each assay individually. Other techniques that would have been virtually impossible are now possible using polynucleotide arrays.

One technique that has been particularly enhanced by the availability of arrays of nucleic acids is sequencing by hybridization (SBH). SBH is a technique for rapidly sequencing nucleic acids without using gels. In SBH, polynucleotides having overlapping sequences are hybridized to a target nucleic acid. The sequences of the polynucleotides that hybridize are then determined and the common sequences overlapped to generate the sequence of the nucleic acid. The use of arrays has allowed the generation of sufficient hybridization information to make SBH feasible on a large scale.

SBH is divided into three formats, depending on the nature of the array and the way in which it is interrogated. In Format I, the target nucleic acid is immobilized and the labeled polynucleotides are in solution. In Format II, the polynucleotides are immobilized and the labeled target nucleic acid is in solution. In Format III, immobilized polynucleotides are hybridized with an unlabeled target nucleic acid and labeled oligonucleotide probes. Hybridization is assayed by ligating the labeled oligonucleotide probes to the immobilized polynucleotides. All three formats require the ability to distinguish perfectly matched hybrids from hybrids that contain a single mismatch at any position. For a more detailed discussion of SBH and the three formats, see WO 98/31836, particularly at pages 1–3.

While the demand for biological arrays, and in particular polynucleotide arrays, is high, current methodologies for constructing such arrays still suffer from certain difficulties. The most common difficulty is assaying the quality and integrity of an array once it has been fabricated. While the chemistries involved in producing the arrays are relatively well understood, methods for synthesizing arrays still suffer from lack of reliability and reproducibility, and even failure. However, identifying regions of attachment failures is very difficult, particularly with the small spots found in miniaturized arrays. Thus, quality control of produced arrays is very difficult to maintain. Furthermore, even minor variations in attachment efficiencies can make interpretation of results generated from such arrays very difficult, as the researcher may not be able to tell whether a difference in signal is real or merely an artifact of the attachment process. This problem is particularly acute in applications such as sequencing by hybridization, which require extremely accurate differentiation of even minor differences in hybridization.

3. SUMMARY OF THE INVENTION

These and other shortcomings in the art are overcome by the present invention, which in one aspect provides spatially addressable arrays of immobilized molecules in which each spot in the array contains an amount of a detectable label which is proportional to the amount of molecule immobilized at that spot. The label can be any molecule which is capable of producing a detectable, quantifiable signal, such as a radioisotope, fluorophore, chromophore, chemiluminescent moiety, etc. The labels at each spot may be the same or different, but are preferably the same.

In another aspect, the invention provides methods of making arrays of immobilized molecules in which each spot in the array contains an amount of a detectable label which is proportional to the amount of molecule immobilized at that spot. In the method, a molecule to be immobilized at a particular spot on the array is "spiked" with a detectable label capable of immobilizing to the substrate with the same efficiency as the molecule. The molecules to be immobilized at different spots are each "spiked" with the same proportion of label. Thus, following immobilization, each spot in the array contains an amount of label which is proportional to the efficiency of the immobilization technique. Following synthesis, the array can be scanned or otherwise analyzed for detectable signal to monitor the fidelity of the array synthesis.

In a preferred embodiment, the label is attached to, incorporated within, or otherwise associated with the same type of molecule as that to be immobilized. Accordingly, in this preferred embodiment of the methods, the molecule to be immobilized is spiked with a small amount of labeled molecule of the same type. Again, the molecules to be immobilized at different locations are each spiked with the same proportion of labeled molecule.

In another aspect, the invention provides methods of increasing the accuracy of array-based assays. In the method, background signals produced from an array of spatially addressable immobilized molecules according to the invention are quantified and recorded.

The array is contacted with a target molecule capable of interacting with at least one of the immobilized molecules. The target molecule is labeled in some manner to produce an assay signal, or the interaction between the target and immobilized molecule is such that only those spots on the array where interaction has taken place produce a detectable assay signal.

Following contact and optional washing, the array is scanned or otherwise analyzed for detectable assay signal, and the signal from each labeled spot quantified. The intensities of the signals from the respective spots are then normalized, typically by obtaining the ratio $I_a/I_b$ (where $I_a$ is the assay signal intensity and $I_b$ is the background signal intensity), to account for signal differences caused by deviations in the quantities of immobilized molecules. This normalization process permits signal intensities from different spots on the array to be directly compared, regardless of the fidelity of the array synthesis.

The labels giving rise to the background signals and assay signals, i.e., the moieties used to label the array spots and target molecules, respectively, may be the same or different. In instances where the same label is used, the background signals should be recorded prior to contacting the array with the target molecule. The assay signal is then obtained by subtracting the background signal from a particular spot from the total signal from that spot. In this embodiment, the assay signals are normalized by obtaining the ratio $(I_a-I_b)/I_b$, where $I_a$ and $I_b$ are as previously defined. When different labels are used, the background signal can be detected and recorded prior to, concomitant with, or after detection of assay signals.

The spatially-addressable arrays and methods of the invention provide myriad advantages over conventional arrays of immobilized molecules. Due to the presence of the labels, the quality of any array can be verified prior to use by simply scanning the array for detectable signal, even in instances where the array is highly miniaturized. Variability in the quantities of molecules immobilized at different positions within the array, and more importantly the complete absence of particular spots from the array, will be readily apparent. Moreover, because the quantity of label at each spot in the array correlates with the quantity of molecule immobilized at that spot, assay signals produced from different spots in the arrays can be normalized and directly compared, regardless of the fidelity of the array synthesis. This feature is particularly important for assays in which signal intensities are critical to determining whether the signal is real.

The advantages of the methods and arrays of the invention are illustrated by way of working examples involving nucleic acid hybridization assays. In the examples, hybridization assays performed with polynucleotide arrays according to the invention were able to discriminate perfectly complementary hybrids from mismatched hybrids which could not be discriminated using conventional polynucleotide arrays.

4. BRIEF DESCRIPTION OF THE FIGURES

5. DETAILED DESCRIPTION OF THE INVENTION

5.1 Definitions

Figure 1:
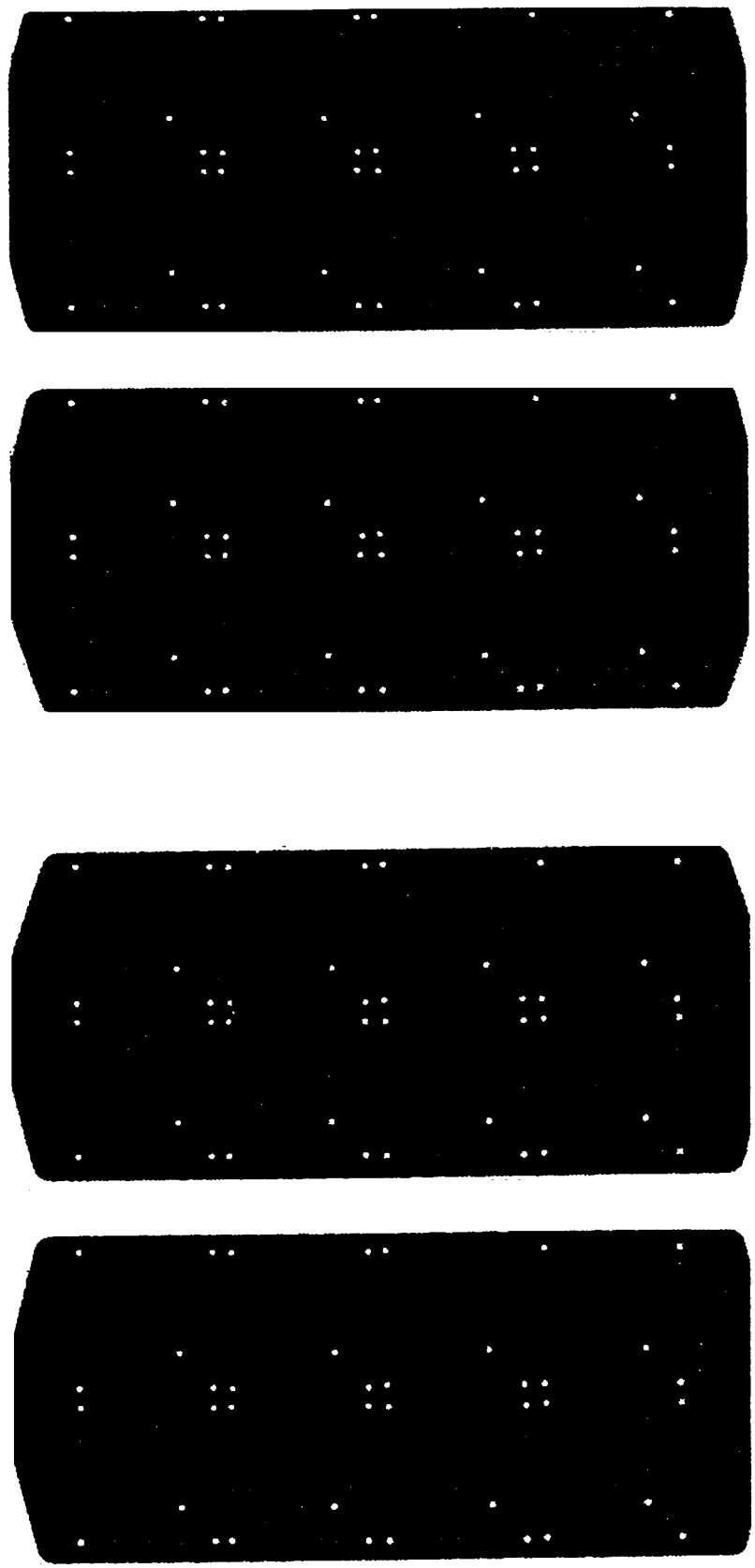
FIG. 1 shows a scan of a polynucleotide array produced with labeled tracer polynucleotides in each polynucleotide mixture. The scan detects the fluorescence at each spot.

As used herein, the following terms shall have the following meanings:

"Spatially addressable array" refers to an array in which each element or component of the array is identifiable by its spatial address, for example its xyz coordinates. Spatial addressable arrays according to the invention can be one dimensional, for example a linear array; two dimensional; or three dimensional.

"Address" or "spot" refers to a particular position in an array. Each address or spot has unique xyz coordinates. The structure of a compound immobilized at a particular address or spot is definable by its coordinates.

"Polynucleotide" refers to a nucleic acid sequence which is immobilized on a substrate. The polynucleotides of the present invention can contain as few as four bases or as many as several hundred or more bases. The polynucleotides can be composed of natural or modified bases or combinations thereof, and can contain one or more modified interlinkages.

"Target nucleic acid" refers to a nucleic acid of known or unknown sequence to be analyzed. The target nucleic acid can be virtually any number of nucleotides in length, but typically is longer than the polynucleotides of the array.

"Tracer moiety" refers to a molecule capable of generating a detectable signal (i.e., a label or labeled molecule) that is or is capable of being immobilized on the spots of the array, and whose amount is proportional to the amount of a molecule of interest immobilized at that spot. The presence of the tracer moiety allows normalization of the array for differences in immobilization efficiencies.

5.2 The Invention

The problems in the art discussed in the Background section are solved by the present invention. The methods of the present invention enable the quality and integrity of arrays of immobilized molecules to be simply and reliably assessed. Quality is assessed by the use of small quantities of labels, either by themselves or attached to the molecules of interest. The labels or labeled molecules are immobilized on the substrate along with the molecules of interest, and their immobilization is proportional to the immobilization of the molecules of interest. The intensity of the signal from the immobilized labels at a given location provides an assessment of the amount of the molecule of interest immobilized on the substrate at that location, and thus provides a way to verify the quality and integrity of the array as a whole. This intensity information is also useful when the array is interrogated, as it provides a way to distinguish real differences in signal intensity due to experimental results from artifactual variations due simply to inconsistent immobilization of the molecules. The invention is also directed to arrays made by these methods and their use in various assay techniques.

The present methods are applicable to a wide variety of different molecules that may be placed in arrays. The methods are particularly exemplified herein in terms of polynucleotides immobilized on a substrate, but they are equally applicable to other types of molecules. For example, one of skill in the art could easily adapt the present methods to apply to other nucleic acids (both DNA and RNA), peptides, polypeptides, proteins, carbohydrates, small biomolecules (e.g. drug candidates), or any other type of molecule that can be immobilized on a substrate by any method. Preferably, the molecule is one that can be labeled, although this is not necessary if a label can be immobilized on the substrate in a fashion similar to the molecule.

The arrays of the present invention may be of any desired size, from two spots to $10^6$ spots or even more. The upper and lower limits on the size of the substrate are determined solely by the practical considerations of working with extremely small or large substrates.

For a given substrate size, the upper limit is determined only by the ability to create and detect the spots in the array. The preferred number of spots on an array generally depends on the particular use to which the array is to be put. For example, sequencing by hybridization will generally require large arrays, while mutation detection may require only a small array. In general, preferred arrays contain from 2 to about $10^6$ spots, more preferably from about 100 to about $10^5$ spots, particularly preferably from about 400 to about $10^4$ spots, and most preferably between about 500 and about 2000 spots.

Furthermore, not all spots on the array need be unique. Indeed, in many applications, redundancies in the spots are desirable for the purposes of acting as internal controls.

A variety of techniques have been described for synthesizing and/or immobilizing arrays of polynucleotides, including in situ synthesis, where the polynucleotides are synthesized directly on the surface of the substrate (see, e.g., U.S. Pat. No. 5,744,305 to Fodor, et al.,) and attachment of pre-synthesized polynucleotides to the surface of a substrate at discrete locations (see, e.g., WO 98/31836). Additional methods are described in WO 98/31836 at pages 41–45 and 47–48, among other places. The present invention is suitable for use with any of these currently available, or later developed, techniques.

In embodiments involving immobilization of pre-synthesized polynucleotides, the polynucleotide reagent to be deposited at a particular spot contains a small quantity, typically 0.01 to 0.15%, and preferably 0.08%, of a label, typically a labeled polynucleotide. The polynucleotide reagent is then deposited on the substrate at a spatially defined region, i.e., at a particular spot. After immobilization, the spot contains an amount of labeled polynucleotide which is proportional to the amount of polynucleotide immobilized at that spot. Depositing a number of such polynucleotide reagents at different spatial addresses yields an array of polynucleotides whose sequences are identifiable by their spatial addresses. Moreover, each spot in the array contains an amount of labeled polynucleotide that is proportional to the amount of polynucleotide immobilized at that spot.

In embodiments involving in situ synthesis of polynucleotides, the polynucleotides are synthesized in their usual manner. At the synthetic step which adds the last nucleotide, the nucleoside phosphoramidite reagent to be deposited contains a small quantity, typically 0.01 to 0.15%, and preferably 0.08%, of a label, typically a labeled nucleoside phosphoramidite. The synthetic scheme yields an array of polynucleotides whose sequences are identifiable by their spatial addresses. Moreover each spot in the array contains an amount of labeled polynucleotide that is proportional to the amount of full-length polynucleotide synthesized at that spot.

While the above method contemplates labeling the last nucleotide of the polynucleotide, those of skill in the art will appreciate that other positions, or additional positions, could be similarly labeled to provide information about the proportions of truncated polynucleotides synthesized. In these embodiments, the labels used at the various steps should be distinguishable from one another.

Moreover, while the in situ synthesis method is described utilizing phosphoramidite reagents, it will be recognized that other reagents utilizing other synthesis strategies can also be employed, and in certain circumstances may be preferable, depending on the stability of the chosen label to the synthesis conditions. Non-limiting examples of suitable chemistries and reagents are described, for example in Oligonucleotide Synthesis: A Practical Approach, M. J. Gait, Ed., IRL Press, Oxford, England, 1985.

The members of the arrays of the invention are immobilized on a solid substrate.

The nature and geometry of the solid substrate will depend upon a variety of factors, including, among others, the type of array (e.g., one-dimensional, two-dimensional or three-dimensional) and the mode of attachment (e.g., covalent or non-covalent). Generally, the substrate can be composed of any material which will permit immobilization of the polynucleotide and which will not melt or otherwise substantially degrade under the conditions used to hybridize and/or denature nucleic acids. In addition, where covalent immobilization is contemplated, the substrate should be activatable with reactive groups capable of forming a covalent bond with the polynucleotide to be immobilized.

A number of materials suitable for use as substrates in the instant invention have been described in the art. Exemplary suitable materials include, for example, acrylic, styrene-methyl methacrylate copolymers, ethylene/acrylic acid, acrylonitrile-butadienestyrene (ABS), ABS/polycarbonate, ABS/polysulfone, ABS/polyvinyl chloride, ethylene propylene, ethylene vinyl acetate (EVA), nitrocellulose, nylons (including nylon 6, nylon 6/6, nylon 6/6–6, nylon 6/9, nylon 6/10, nylon 6/12, nylon 11 and nylon 12), polycarylonitrile (PAN), polyacrylate, polycarbonate, polybutylene terephthalate (PBT), polyethylene terephthalate (PET), polyethylene (including low density, linear low density, high density, cross-linked and ultra-high molecular weight grades), polypropylene homopolymer, polypropylene copolymers, polystyrene (including general purpose and high impact grades), polytetrafluoroethylene (PTFE), fluorinated ethylene-propylene (FEP), ethylene-tetrafluoroethylene (ETFE), perfluoroalkoxyethylene (PFA), polyvinyl fluoride (PVF), polyvinylidene fluoride (PVDF), polychlorotrifluoroethylene (PCTFE), polyethylene-chlorotrifluoroethylene (ECTFE), polyvinyl alcohol (PVA), silicon styreneacrylonitrile (SAN), styrene maleic anhydride (SMA), metal oxides and glass.

The substrate may be in the form of beads, particles or sheets, and may be permeable or impermeable, depending on the type of array. For example, for linear or three-dimensional arrays the substrate may consist of bead or particles (such as conventional solid phase synthesis supports), fibers (such as glass wool or other glass or plastic fibers) or glass or plastic capillary tubes. For two-dimensional arrays, the substrate is preferably in the form of plastic or glass sheets in which at least one surface is substantially flat. Particularly preferred substrates for use with two-dimensional arrays are glass slides.

The composition of the immobilized polynucleotides is not critical. The only requirement is that they be capable of hybridizing to a target nucleic acid of complementary sequence. For example, the polynucleotides may be composed of all natural or all synthetic nucleotide bases, or a combination of both. Non-limiting examples of modified bases suitable for use with the instant invention are described, for example, in Practical Handbook of Biochemistry and Molecular Biology, G. Fasman, Ed., CRC Press, 1989, pp. 385–392. While in most instances the polynucleotides will be composed entirely of the natural bases (A, C, G, T or U), in certain circumstances the use of synthetic bases may be preferred.

Moreover, while the backbones of the polynucleotides will typically be composed entirely of "native" phosphodiester linkages, they may contain one or more modified linkages, such as one or more phosphorothioate, phosphoramidite or other modified linkages. As a specific example, one or more immobilized polynucleotides may be a peptide nucleic acid (PNA), which contains amide interlinkages. Additional examples of modified bases and backbones that can be used in conjunction with the invention, as well as methods for their synthesis can be found, for example, in Uhlman & Peyman, 1990, Chemical Review 90(4):544–584; Goodchild, 1990, Bioconjugate Chem. 1(3):165–186; Egholm et al., 1992, J. Am. Chem. Soc. 114:1895–1897; Gryaznov et al., J. Am. Chem. Soc. 116:3143–3144, as well as the references cited in all of the above.

While the immobilized polynucleotides will in most instances be a contiguous stretch of nucleotides, they need not be. Stretches of nucleotides can be interrupted by one or more linker molecules that do not participate in sequence-specific base pairing interactions with a target nucleic acid. The linker molecules may be flexible, semi-rigid or rigid, depending on the desired application. A variety of linker molecules useful for spacing one molecule from another or from a solid surface have been described in the art (and are described more thoroughly infra); all of these linker molecules can be used to space regions of immobilized polynucleotides from one another. In a preferred embodiment of this aspect of the invention, the linker moiety is from one to ten, preferably one to six, alkylene glycol moieties, preferably ethylene glycol moieties.

The immobilized polynucleotides may be as few as four, or as many as hundreds, or even more, nucleotides in length. Specifically contemplated as polynucleotides according to the invention are nucleic acids that are typically referred to in the art as oligonucleotides and also those referred to as nucleic acids. Thus, the arrays of the present invention are useful not only in applications where target nucleic acids are hybridized to immobilized arrays of relatively short (i.e., 6–20 nucleotide) probes (such as format II SBH), but also in applications where relatively short probes are hybridized to arrays of immobilized nucleic acids.

The polynucleotides of the array can be of any desired sequence. In a preferred embodiment, they can comprise all possible polynucleotides of a given length N, which would result in an array of $4^N$ unique elements. For all polynucleotides of, for example, 6 bases in length, the sequences would comprise an array with 4096 unique elements.

Alternatively, the polynucleotides can make up the "universal set" for sequencing a nucleic acid, as discussed in WO 98/31836, particularly pages 27–29.

In an alternative embodiment, the set of polynucleotides may correspond to particular mutations that are to be identified in a known sequence. For example, if a particular nucleic acid is known to contain an unidentified mutation at a particular position, then the mutated position can be identified with an array of eight polynucleotides, three corresponding to the three possible substitutions at that position, one corresponding to the deletion of the base at that position, and four corresponding to the insertion of the four possible bases at that position. Alternatively, for a known gene that may contain any of several possible identified mutations, the array can comprise polynucleotides corresponding to the different possible mutations. This embodiment is particularly useful for genes like oncogenes and tumor suppressors, which frequently have a variety of known mutations in different positions. Using arrays facilitates determining whether or not these genes contain mutations by allowing simultaneous screening with polynucleotides corresponding to each of these different positions.

In another alternative embodiment, each spot of the array can comprise a mixture of polynucleotides of different sequences. These mixtures may comprise degenerate polynucleotides of the structure $N_x B_y N_z$, wherein N represents any of the four bases and varies for the polynucleotides in a given mixtures, B represents any of the four bases but is the same for each of the polynucleotides in a given mixture, and x, y, and z are integers.

Arrays comprising this type of mixture are useful in, for example, sequencing by hybridization. Alternatively, the spots may comprise mixtures of polynucleotides that correspond to different regions of a known nucleic acid; these regions may be overlapping, adjacent, or nonadjacent. Arrays comprising these types of mixtures are useful in, for example, identifying specific nucleic acids, including those from particular pathogens or other organisms. Both types of mixtures are discussed in WO 98/31836, particularly at pages 123–128.

The polynucleotides can be isolated from biological samples, generated by PCR reactions or other template-specific reactions, or made synthetically. Methods for isolating polynucleotides from biological samples and/or PCR reactions are well-known in the art, as are methods for synthesizing and purifying synthetic polynucleotides. Probes isolated from biological samples and/or PCR reactions may, depending on the desired mode of immobilization, require modification at the 3'- or 5'-terminus, or at one or more bases, as will be discussed more thoroughly below. Moreover, since the polynucleotide must be capable of hybridizing to a target nucleic acid, if not already single stranded, it should preferably be rendered single stranded, either before or after immobilization on the substrate.

The polynucleotides can be immobilized on the substrate using a wide variety of techniques. For example, the polynucleotides can be adsorbed or otherwise non-covalently associated with the substrate (for example, immobilization to nylon or nitrocellulose filters using standard techniques); they may be covalently attached to the substrate; or their association may be mediated by specific binding pairs, such as biotin and streptavidin. Of these methods, covalent attachment is preferred.

In order to effect covalent attachment, the substrate must first be activated, i.e., treated so as to create reactive groups on or within the substrate that can react with a reactive group on the polynucleotide to form a covalent linkage. Those of skill in the art will recognize that the desired reactive group will depend on the chemistry used to attach the polynucleotides to the substrate and the composition of the substrate. Typical reactive groups useful for effecting covalent attachment of polynucleotides to substrates include hydroxyl, sulfonyl, amino, epoxy, isothiocyanate and carboxyl groups; however, other reactive groups as will be apparent to those having skill may also be used and are also included within the scope of the invention.

For a review of the myriad techniques that can be used to activate the substrates with suitable reactive groups, see Wiley Encyclopedia of Packaging Technology, 2d Ed., Brody & Marsh, Ed., "Surface Treatment," pp. 867–874, John Wiley & Sons (1997), and the references cited therein (hereinafter "Surface Treatment"). Chemical methods suitable for generating amino groups on silicon oxide substrates are described in Atkinson & Smith, "Solid Phase Synthesis of Oligodeoxyribonucleotides by the Phosphite Triester Method," In: Oligonucleotide Synthesis: A Practical Approach, M J Gait, Ed., 1984, IRL Press, Oxford, particularly at pp. 45–49 (and the references cited therein); chemical methods suitable for generating hydroxyl groups on silicon oxide substrates are described in Pease et al., 1994, Proc. Natl. Acad. Sci. USA 91:5022–5026 (and the references cited therein); chemical methods for generating functional groups on polymers such as polystyrene, polyamides and grafted polystyrenes are described in Lloyd-Williams et al., 1997, Chemical Approaches to the Synthesis of Peptides and Proteins, Chapter 2, CRC Press, Boca Raton, Fla. (and the references cited therein).

Those of skill in the art will recognize that in embodiments employing covalent attachment, the covalent bond formed between the polynucleotide and the substrate must be substantially stable to the various conditions under which the array will be assayed, to avoid loss of polynucleotide during the assay. One such stable bond is the phosphodiester bond, which connects the various nucleotides in a polynucleotide, and which can be conveniently formed using well-known chemistries (see, e.g., Oligonucleotide Synthesis: A Practical Approach, 1984, supra). Other stable bonds suitable for use with hydroxyl-activated substrates include phosphorothioate, phosphoramidite, or other modified nucleic acid interlinkages. For substrates modified with amino groups, the bond could be a phosphoramidate, amide or peptide bond. When substrates are activated with epoxy functional groups, a stable C—N bond could be formed. Suitable reagents and conditions for forming such stable bonds are well known in the art. Other stable bonds suitable for use with the arrays of the invention will be apparent to those of skill in the art.

In embodiments in which pre-synthesized polynucleotides are covalently attached to the substrate, the polynucleotides may be via their 3'-terminus, 5'-terminus or by way of a reactive group at one of the bases. Synthesis supports and synthesis reagents useful for modifying the 3'- and/or 5'-terminus of synthetic polynucleotides, or for incorporating a base modified with a reactive group into a synthetic polynucleotide, are well-known in the art and are also commercially available.

For example, methods for synthesizing 5'-modified polynucleotides are described in Agarwal et al., 1986, Nucl. Acids Res. 14:6227–6245 and Connelly, 1987, Nucl. Acids Res. 15:3131–3139. Commercially available products for synthesizing 5'-amino modified polynucleotides include the N-TFA-C6-AminoModiferm, N-MMT-C6-AminoModiferm and N-MMT-C12-AminoModifierm reagents available from Clontech Laboratories, Inc., Palo Alto, California.

Methods for synthesizing 3'-modified polynucleotides are described in Nelson et al., 1989, Nucl. Acids Res. 17:7179–7186 and Nelson et al., 1989, Nucl. Acids Res. 17:7187–7194. Commercial products for synthesizing 3'-modified polynucleotides include the 3'-Amino-ON™ controlled pore glass and Amino Modifier II™ reagents available from Clontech Laboratories, Inc., Palo Alto, Calif.

Other methods for modifying the 3' and/or 5' termini of polynucleotides, as well as for synthesizing polynucleotides containing appropriately modified bases are provided in Goodchild, 1990, Bioconjugate Chem. 1:165–186, and the references cited therein. Chemistries for attaching such modified polynucleotides to substrates activated with appropriate reactive groups are well-known in the art (see, e.g., Ghosh & Musso, 1987, Nucl. Acids Res. 15:5353–5372; Lund et al., 1988, Nucl. Acids Res. 16:10861–10880; Rasmussen et al., 1991, Anal. Chem. 198:138–142; Kato & Ikada, 1996, Biotechnology and Bioengineering 51:581–590; Timofeev et al., 1996, Nucl. Acids Res. 24:3142–3148; O'Donnell et al., 1997, Anal. Chem. 69:2438–2443).

Methods and reagents for modifying the ends of polynucleotides isolated from biological samples and/or for incorporating bases modified with reactive groups into nascent polynucleotides are also well-known and commercially available. For example, an isolated polynucleotide can be phosphorylated at the 5'-terminus with phosphorokinase and this phosphorylated polynucleotide covalently attached to an amino-activated substrate through a phosphoramidate or phosphodiester linkage. Other methods will be apparent to those of skill in the art.

In one convenient embodiment, pre-synthesized polynucleotides, modified at their 3'- or 5'-termini with a primary amino group, are conjugated to a carboxy-activated substrate. Chemistries suitable for forming carboxamide linkages between carboxyl and amino functional groups are well-known in the art of peptide chemistry (see, e.g., Atherton & Sheppard, Knorr et al., 1989, Tet. Lett. 30(15): 1927–1930; Bannworth & Knorr, 1991, Tet. Lett. 32(9): 1157–1160; and Wilchek et al., 1994, Bioconjugate Chem. 5(5):491–492; Solid Phase Peptide Synthesis, 1989, IRL Press, Oxford, England and Lloyd-Williams et al., Chemical Approaches to the Synthesis of Peptides and Proteins, 1997, CRC Press, Boca Raton, FL and the references cited therein). Any of these methods can be used to conjugate amino-modified polynucleotides to a carboxy-activated substrate.

In another convenient embodiment, the polynucleotides are synthesized directly on a hydroxy-activated substrate using commercially available phosphoramidites synthesis reagents. In this mode, the polynucleotides are covalently attached to the substrate via their 3'-termini by way of a phosphodiester linkage. Alternatively, photoprotected phosphoramidites and the photolithographic methods described in U.S. Pat. No. 5,744,305 to Fodor et al. and Pease et al., 1994, supra, can be used.

Whether synthesized directly on the activated substrate or immobilized on the activated substrate after synthesis or isolation, the polynucleotides can optionally be spaced away from the substrate by way of one or more linkers. As will be appreciated by those having skill in the art, such linkers will be at least bifunctional, i.e., they will have one functional group or moiety capable of forming a linkage with the activated substrate and another functional group or moiety capable of forming a linkage with another linker molecule or the polynucleotides. The linkers may be long or short, flexible or rigid, charged or uncharged, hydrophobic or hydrophilic, depending on the particular application.

In certain circumstances, such linkers can be used to "convert" one functional group into another. For example, an amino-activated substrate can be converted into a hydroxyl-activated substrate by reaction with, for example, 3-hydroxy-propionic acid. In this way, substrate materials which cannot be readily activated with a specified reactive functional group can be conveniently converted into an appropriately activated substrate. Chemistries and reagents suitable for "converting" such reactive groups are well-known, and will be apparent to those having skill in the art.

Linkers can also be used, where necessary, to increase or "amplify" the number of reactive groups on the activated substrate. For this embodiment, the linker will have three or more functional groups. Following attachment to the activated substrate by way of one of the functional groups, the remaining two or more groups are available for attachment of polynucleotides. Amplifying the number of functional groups on the activated substrate in this manner is particularly convenient when the substrate cannot be readily activated with a sufficient number of reactive groups.

Reagents for amplifying the number of reactive groups are well-known and will be apparent to those of skill in the art. A particularly convenient class of amplifying reagents are the multifunctional epoxides sold under the trade name DENACOL™ (Nagassi Kasei Kogyo K. K.). These epoxides contain as many as four, five, or even more epoxy groups, and can be used to amplify substrates activated with reactive groups that react with epoxides, including, for example, hydroxyl, amino and sulfonyl activated substrates. The resulting epoxy-activated substrate can be conveniently converted to a hydroxyl-activated substrate, a carboxy-activated substrate, or other activated substrate by well-known methods.

Linkers suitable for spacing biological molecules such as polynucleotides from solid surfaces are well-known in the art, and include, by way of example and not limitation, polypeptides such as polyproline or polyalanine, saturated or unsaturated bifunctional hydrocarbons such as 1-amino-hexanoic acid, polymers such as polyethylene glycol, etc. 1,4-Dimethoxytrityl-polyethylene glycol phosphoramidites useful for forming phosphodiester linkages with hydroxyl groups, as well as methods for their use in nucleic acid synthesis on solid substrates, are described, for example in Zhang et al., 1991, Nucl. 20 Acids Res. 19:3929–3933 and Durand et al., 1990, Nucl. Acids Res. 18:6353–6359. Other useful linkers are commercially available.

A critical feature of the arrays of the invention is the presence of an amount of a label at each position within the array that is proportional to the amount of polynucleotide immobilized at that particular spot. Thus, it is important that the efficiencies of the coupling reactions which are used to immobilize the label and polynucleotide are substantially similar. For covalent attachment, this can be conveniently achieved by using the same immobilization reactive group on both the label and the polynucleotide.

For embodiments employing immobilization of pre-synthesized polynucleotides, a preferred label is a labeled polynucleotide. The primary sequences of the labeled and unlabeled polynucleotides at a particular spot may be the same or different. In fact, the same labeled polynucleotide may be used at each spot in the array. The only requirement is that the polynucleotide reagents deposited at each spot in the array be "spiked" with substantially the same proportion of labeled polynucleotide.

In a preferred embodiment, the same mixture of labeled polynucleotides is used to spike the polynucleotide reagent deposited at each spot. Using the same mixture of labeled polynucleotides at each spot ensures that the labels at different spots do not induce sequence-specific anomalies in hybridization assays, i.e., it ensures that the labels at each array spot interact similarly with a target nucleic acid in hybridization assays. Moreover, use of the same label at each spot reduces the number of labeled polynucleotides that need to be prepared. A particularly preferred mixture of ten labeled polynucleotides is described in the examples section.

Virtually any label that produces a detectable, quantifiable signal and that is capable of being immobilized on a substrate or attached to a polynucleotide can be used in conjunction with the arrays of the invention. Suitable labels include, by way of example and not limitation, radioisotopes, fluorophores, chromophores, chemiluminescent moieties, etc. In embodiments where the label is attached to a polynucleotide, the label can be attached to any part of the polynucleotide, including the free terminus or one or more of the bases. Preferably, the position of the label will not interfere with hybridization, detection or other post-hybridization modifications of the labeled polynucleotide. Suitable methods of making labeled polynucleotides are well known in the art.

Due to their ease of detection, polynucleotides labeled with fluorophores are preferred. Fluorophores suitable for labeling polynucleotides are described, for example, in the Molecular Probes catalog (Molecular Probes, Inc., Eugene Oreg. 97402–9144), and the references cited therein. Methods for attaching fluorophore labels to polynucleotides are well known, and can be found, for example in Goodchild, 1990, supra. A preferred fluorophore label is the carboxylic acid of tetramethyl rhodaimine (TAMRA dye), which is available from Molecular Probes.

In embodiments employing in situ synthesis, a preferred label is a fluorescentlylabeled nucleic acid synthesis reagent, such as a labeled nucleoside phosphoramidite. The position at which the fluorophore is attached to the nucleoside phosphoramidite will depend on whether the label will be added at the terminal or internal nucleotides of the nascent polynucleotides. When a terminal label is desired, the fluorophore can be conveniently attached to the 5'-hydroxyl. When internal labels are desired, the flurophore is preferably attached to the base, optionally by way of a linker. Methods suitable for making fluorescently-labeled phosphoramidite synthesis reagents are well-known in the art, and are described, for example, in Goodchild, 1990, supra.

The amount of label used to "spike" the polynucleotide reagent to be deposited at a particular spot is not critical for success. However, the amount used should be sufficient to produce a detectable signal which does not result in a loss of dynamic range when the array is used in an assay. For the preferred polynucleotide arrays of the invention, which are synthesized by depositing pre-synthesized polynucleotides at discrete spots, it has been found that spiking the polynucleotide reagent with about 0.01 to 0.15%, preferably about 0.08%, of a fluorescently-labeled polynucleotide yields good results. When mixtures of fluorescently-labeled polynucleotides are used, the total quantity of labeled polynucleotides used to spike the reagent should fall within the above-described ranges.

The polynucleotide arrays according to the invention can be used in virtually any array in which hybridization is desirable. For example, the polynucleotide arrays of the invention are useful for all three formats of sequencing by hybridization, as well as the myriad other hybridization arrays performed with arrays of nucleic acids and/or oligo-nucleotide probes described in the art.

For use in a hybridization array, the background signals from a polynucleotide array according to the invention are quantified and recorded. The mode of detection will depend on the nature of the label. For flourescent labels, the background signals can be conveniently quantified by scanning the array with a confocal camera or with a CCD camera, as is well-known in the art.

Use of the arrays of the present invention contemplates the use of either probe polynucleotides or target nucleic acids that are capable of generating a signal when appropriately hybridized to the array. The probe polynucleotides or target nucleic acids may be labeled, for example, by the labels and techniques described supra for labeling the tracer polynucleotide. Alternatively, they may be labeled by any other technique known in the art. Preferred techniques include direct chemical labeling methods and enzymatic labeling methods, such as kinasing and nick-translation.

The array is contacted with a target nucleic acid, which may be labeled or unlabeled, depending on the particular array (for example, format II vs. format III SBH), under conditions which discriminate between perfectly complimentary hybrids and hybrids containing one or more mismatches. The actual hybridization conditions used will depend upon, among other factors, the G+C content of the sequence of interest and the lengths of the immobilized polynucleotides comprising the array. Hybridization conditions useful for discriminating between perfect compliments and mismatches for a variety of hybridization arrays have been described in the art. For example, hybridization conditions useful for discriminating complimentary and mismatched hybrids in a variety of SBH and other applications are described in U.S. Pat. No. 5,525,464 to Drmanac et al., WO 95/09248 and WO 98/31836. A particularly detailed discussion of the theoretical and practical considerations involved in determining hybridization conditions, and including a discussion of the advantages of low-temperature washing steps, may be found in WO 98/31836, particularly pages 50–62. Additional guidance may be found in Harmes and Higgins, Nucleic Acid Hybridization: A Practical Approach, 1985, IRL Press, Oxford, England.

Following contact, the array is optionally washed, typically under moderate- to high stringency conditions to remove unhybridized target. If the target is labeled, the array can be scanned or otherwise analyzed for detectable assay signal, and the signal from each labeled spot, or alternatively from all spots, quantified. Only those spots where hybridization occurred will produce a detectable assay signal. If each spot in array contains the same quantity of immobilized polynucleotide, in theory, the intensity of the assay signal at each spot will be proportional to the extent of hybridization at that spot. For example, spots containing perfectly complementary hybrids are expected to produce more intense assay signals than spots containing mismatched hybrids. In practice, however, differences in signal intensities between different spots may instead be due to differences in the amounts of polynucleotide immobilized at the respective spots.

Because each spot in the arrays of the invention contain an amount of a label or "tracer" proportional to the amount of polynucleotide immobilized at the particular spot, the assay signals obtained from the arrays of the invention can be normalized. As a consequence, signal intensities from spots within a single array, or across multiple arrays, can be directly compared, without regard to the fidelity of the particular array synthesis.

The method by which the signals are normalized will depend upon whether the tracer or background signals are the same as the assay signals, such as where the polynucleotides and target nucleic acid are labeled with the same fluorophore. In this embodiment, a normalized signal of a particular spot is defined by $(I_a-I_b)/I_b$, where $I_a$ is the intensity of the assay signal of the spot (i.e., intensity of the spot after hybridization) and $I_b$ is the intensity of the background signal of the spot (i.e., the intensity of the spot before hybridization).

In embodiments where the background and assay signals are different, i.e., where the array spots and target nucleic acid are labeled with different fluorophores, the normalized signal for a spot is described by $I_a/I_b$, where $I_a$ is the intensity of the assay signal of the spot and $I_b$ is the intensity of the background signal of the same spot.

While the array is illustrated utilizing a labeled target nucleic acid, those of skill in the art will recognize that the arrays of the invention are also useful in assays employing unlabeled target nucleic acids, such as assays employing the principles of format III SBH. The only requirement is that some component of the particular assay generate a detectable signal at spots where hybridization occurs.

6. EXAMPLE
Tracer Labeling of a Polynucleotide Array

An array of polynucleotides was generated using the surface of a glass slide as the substrate. The polynucleotides used were 8 bases long, with an information content corresponding to all possible 5-base sequences. The polynucleotides all had the structure 5'-36C(spacer)-NNNBBBBB-3', where:

36C(spacer) is a standard, commercially available 36 carbon spacer element;

N represents a degenerate position generated by synthesizing the polynucleotide with an equimolar mixture of all four bases according to standard methods (i.e., each location on the array contained a mixture of polynucleotides degenerate at the N positions); and B represents any one of the four bases (i.e., each location on the array contained a mixture of polynucleotides identical at the B positions).

For the methods of the invention, a mixture of 10 labeled polynucleotide mixtures was prepared. The polynucleotides in the 10 mixtures had the structure describe above, and the labeled mixture consisted of the following sequences:

NNNGGCAT NNNCGGAG NNNAACTG NNNATGAA NNNTGTAC

NNNACTGG NNNGAACC NNNTACAG NNNCTGGA NNNCCGGA

Each of these polynucleotide mixtures was labeled at its 3' end with TAMRA dye (Molecular Probes, Eugene, Oreg.). TAMRA dye has an absorption maximum at 565 nm and an emission maximum at 580 nm; its molecular extinction coefficient is 89,000.

The glass slide was prepared for attachment of the polynucleotides of the array by generating isothiocyanate groups (—N=C—S) on the surface of the slide. The slide was derivatized with isothiocyanate groups according to the following protocol:

(1) Soak glass slide in 1 M HCl for 16 hr. (Alternatively, soak in 1 M nitric acid for 3 hr.) Rinse thoroughly with deionized water, followed by acetone. Allow to air dry.

(2) Soak slide in hexane, acetone, and methanol, respectively, for 10 min each. Air dry when done. The slide must be completely dry before proceeding to the next step.

(3) Prepare a solution containing 2% aminopropyltriethoxy silane in 95% acetone:water in a plasic container and let stand 10 min to activate. Submerge slide in this silane solution for about 2 min and immediately rinse with acetone. Wash slide with 3 consecutive acetone washes. Allow to completely air dry.

(4) Cure slides by baking in a dry incubator at 98 C for 45 min. Remove from incubator and allow to cool for at least 10 min.

(5) Dissolve 1,4-phenylene diisothiocyanate (PDC) in a 10% solution of pyridine:dimethyl formamide to yield a final concentration of 0.2% PDC. Submerge the slide in the PDC solution and incubate for 2 hr at room temperature. Remove the slide and wash by submerging in methanol for 5 min, followed by two successive baths of acetone for 5 min each. Allow slide to air dry.

For each spot of the array, small volumes of polynucleotides mixtures containing 50 $\mu$M of the particular degenerate polynucleotide pool for that spot and 0.04 $\mu$M of the labeled polynucleotide mix (0.08% of the total concentration) were prepared. These mixtures were then spotted onto the prepared slide using a robotic pin spotting device. The spotted polynucleotides covalently bonded to the surface of the slide through a bond between the cyanate molecule on the slide and the 5' amine of the polynucleotide.

Before assaying the array, the baseline level of fluorescence at each location in the array was established by scanning the array to detect the amount of labeled tracer polynucleotide at each spot (FIG. 1).

Figure 2:
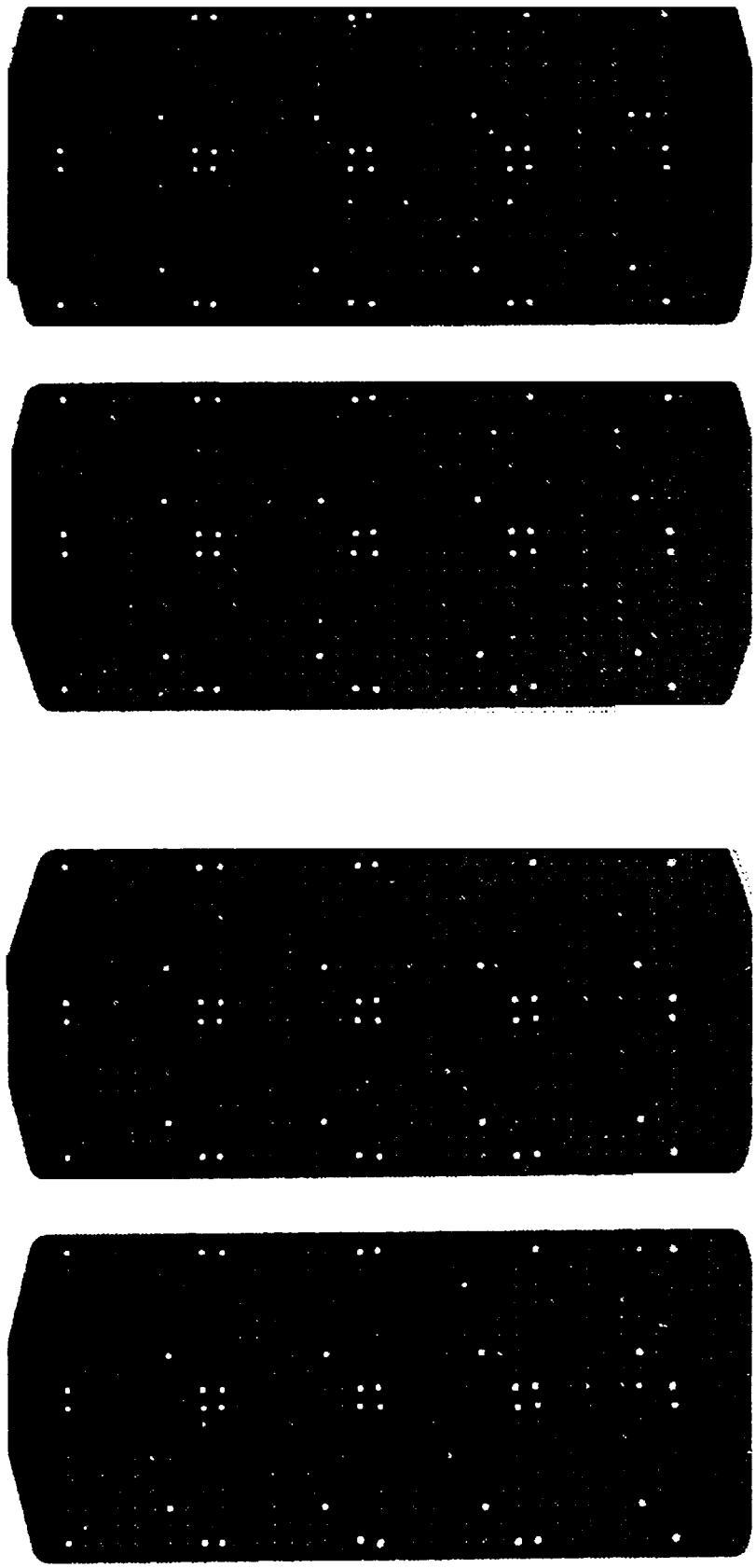
FIG. 2 shows a scan of the array of FIG. 1 after hybridization and ligation with the target DNA and labeled polynucleotides.

The array was then assayed with a 241 base, single-stranded target DNA derived from exon 7 of the p53 gene and selected sets of TAMRA dye-labeled 5-base polynucleotides. After allowing the target DNA, attached polynucleotides, and labeled polynucleotides to hybridize under conditions intended to discriminate between perfect matches and single-base mismatches, ligase was added. The ligase covalently joined labeled polynucleotides to attached polynucleotides in the spots of the array at which they bound the target DNA in adjacent positions. The arrays were then washed to remove the target DNA and unligated labeled polynucleotides. The array was again scanned to determine the total fluorescent signal at each position on the array (FIG. 2).

The intensity signals from each spot on the probed array were then normalized to the baseline signals from the corresponding spot on the array, to account for differences in polynucleotide attachment efficiency. The intensities were normalized according to the formula $(I_a-I_b)/I_b$, where $I_a$ is the assay signal intensity and $I_b$ is the background signal intensity. The normalized intensities were then used to identify mutations in the p53 gene by discriminating between perfect complements and mismatches.

As a control, the same assay was also performed on an array generated by the same protocol as the labeled array, but without the use of the labeled polynucleotide tracer mixtures. Because it lacked the tracer in the spots of the array, the intensities could not be normalized for the attachment of the polynucleotides.

When the results from the two assays were compared, the signals from the array with the tracer (which could be normalized for the efficiency of attachment at each spot) led to the detection of the mutation in the p53 gene, while the signals from the array without the tracer (which could not be normalized for the efficiency of attachment at each spot) could not.

The present invention is not to be limited in scope by the exemplified embodiments which are intended as illustrations of single aspects of the invention The foregoing specification and accompanying drawings is considered to be sufficient to enable one skilled in the art to broadly practice the invention. Indeed, various modifications of the above-described means for carrying out the invention which are obvious to those skilled in the relevant arts are intended to be within the scope of the following claims. All patents, patents applications, and publications cited herein are hereby incorporated by reference in their entireties for all purposes.

What is claimed is:

1. A spatially-addressable array of compounds, comprising a substrate having directly attached thereon, optionally by a linker at each of a plurality of distinct addresses a compound and a tracer moiety, wherein the structures of the compounds are identifiable by their spatial addresses, and wherein the amount of the tracer moiety attached at each address is proportional to the amount of compounds attached at that address.

2. The array of claim 1 which is a one-dimensional array.

3. The array of claim 2 in which the substrate is a solid-phase synthesis support, a glass fiber or a capillary tube.

4. The array of claim 1 which is a two-dimensional array.

5. The array of claim 1 in which the substrate is a glass or plastic sheet.

6. The array of claim 1, in which the directly attached compounds are polynucleotides.

7. The array of claim 6 in which the polynucleotides are covalently attached to the substrate, optionally by way of a linker.

8. The array of claim 7, in which the polynucleotides are covalently attached to the substrate via their 5' or 3' terminal nucleotide.

9. The array of claim 7 which comprises 10 to $10^6$ different polynucleotides.

10. The array of claim 7 in which each immobilized polynucleotide is independently 6 to 20 nucleotides in length.

11. The array of claim 10, in which all of the directly attached polynucleotides are the same length.

12. The array of claim 10, which comprises a complete set of polynucleotides 6–10 nucleotides in length.

13. The array of claim 6 in which the polynucleotide directly attached, optionally by a linker, at one or more address is a mixture of polynucleotides.

14. The array of claim 13, in which the polynucleotide directly attached, optionally by a linker, at each address is a mixture of polynucleotides.

15. The array of claim 13 or 14, in which the mixture is of the formula: $N_xB_yN_z$, wherein each N represents any of the five encoding bases and varies for the polynucleotides in a given mixtures, B represents any of the five encoding bases and is the same for each of the polynucleotides in a given mixture, and x, y, and z are each independently integers.

16. The array of claim 1 in which the tracer moiety comprises a fluorophore.

17. The array of claim 6 in which the tracer moiety is a fluorescently-labeled polynucleotide.

18. The array of claim 17 in which the fluorescently-labeled polynucleotide directly attached, optionally by a linker, at each address has the same nucleotide sequence as the polynucleotide directly attached, optionally by a linker at that address.

19. The array of claim 17 in which the fluorescent label is TAMRA.

20. The array of claim 17, in which the same fluorescently-labeled polynucleotide is directly attached, optionally by a linker, at each address.

21. The array of claim 20, in which the fluorescently-labeled polynucleotide comprises a mixture of fluorescently-labeled polynucleotides.

22. The array of claim 21, in which the mixture of fluorescently labeled polynucleotides comprises:

NNNGGCAT-F,

NNNCGGAG-F,

NNNAACTG-F,

NNNATGAA-F,

NNNTGTAC-F,

NNNACTGG-F,

NNNGAACC-F,

NNNTACAG-F,

NNNCTGGA-F, and

NNNCCGGA-F, wherein each N represents any of the five encoding bases and F is a fluorophore.

23. The array of claim 22, in which F is TAMRA.

24. A method of making a spatially-addressable array of compounds, comprising the steps of:

(i) directly attaching, optionally by a linker, at a first address of a substrate a first compound and a first tracer moiety; and (ii) directly attaching, optionally by a linker, a second address of a substrate a second compound and a second tracer moiety.

25. In a method of making spatially addressable array of polynucleotides by directly attaching, optionally by a linker pre-synthesized polynucleotides at a discrete spatial address on a substrate, the improvement comprising directly attaching, optionally by a linker an amount of a tracer moiety at each spatial address that is proportional to the amount of polynucleotide attached at that address.

26. In a method of making a spatially addressable array of compounds by in situ synthesis, the improvement comprising directly attaching optionally by a linker at each spatial address of the array an amount of a tracer moiety that is proportional to the amount of a product of the in situ synthesis directly attached, optionally by a linker, at that address.

27. A method of increasing the accuracy of an array-based assay comprising:

contacting an array according to claim 1 with a an analyte compound that is capable of generating an assay signal upon interacting with a compound of the array; and normalizing the assay signals to account for differences in the amounts of compounds immobilized at different addresses in the array, thereby increasing the accuracy of the assay.

28. The method of claim 27 in which the assay signals are normalized by obtaining the ratio of the assay signal intensity at an address to the background signal intensity at that address.

29. The method of claim 28 in which the background signal intensity at an address is obtained by measuring the signal intensity of that address prior to contacting the array with the analyte compound.

30. A method of normalizing hybridization signals in an array-based hybridization experiment, comprising the steps of:

contacting an array of immobilized polynucleotides according to claim 6 with a target nucleic acid under conditions in which addresses of the array bearing immobilized polynucleotides that are complimentary to a region of the target nucleic acid produce a detectable hybridization signal; and normalizing the hybridization signal at an address by obtaining the ratio of the hybridization signal intensity at the address to the background signal intensity at that address.

31. The method of claim 30 in which the background signal intensity of the address is obtained by measuring the signal intensity at the address prior to contacting the array with the target nucleic acid.

32. The method of claim 30 in which the target nucleic acid is labeled.

33. The method of claim 30 in which the array is further contacted with a set of labeled solution-phase polynucleotide probes and labeled probes and array polynucleotides that hybridize adjacently to the same target nucleic acid molecule are covalently joined.

\* \* \* \* \*